United States Patent [19]

Mattson et al.

[11] 3,954,976

[45] May 4, 1976

[54] PHARMACEUTICAL COMPOSITIONS FOR INHIBITING ABSORPTION OF CHOLESTEROL

[75] Inventors: Fred Hugh Mattson; Robert Anthony Volpenhein, both of Cincinnati, Ohio

[73] Assignee: The Procter & Gamble Company, Cincinnati, Ohio

[22] Filed: Dec. 14, 1973

[21] Appl. No.: 425,010

[52] U.S. Cl. ................................................ 424/180
[51] Int. Cl.² ......................................... A01N 9/00
[58] Field of Search ................................... 424/180

[56] References Cited
UNITED STATES PATENTS

| | | | |
|---|---|---|---|
| 2,893,990 | 7/1959 | Hass et al. | 260/234 |
| 2,962,419 | 11/1960 | Minich | 167/81 |
| 3,849,554 | 11/1974 | Winitz | 424/180 |

*Primary Examiner*—Elbert L. Roberts
*Attorney, Agent, or Firm*—Richard C. Witte; Julius P. Filcik; Jerry J. Yetter

[57] ABSTRACT

Pharmaceutical compositions for inhibiting the absorption of cholesterol comprising effective unit dosage amounts of a polyol fatty acid ester having at least four fatty acid ester groups; and a method for treating and/or preventing hypercholesterolemia in an animal comprising systematically administering to such animal successive therapeutically effective doses of said polyol fatty acid ester.

9 Claims, No Drawings

PHARMACEUTICAL COMPOSITIONS FOR INHIBITING ABSORPTION OF CHOLESTEROL

BACKGROUND OF THE INVENTION

1. Field of the Invention

This invention relates to novel compositions having therapeutic effects. The invention further relates to a novel method for treating or preventing hypercholesterolemia in animals.

2. The Prior Art

Pathological conditions which can afflict warmblooded animals can involve the absorption of cholesterol, and associated hypercholesterolemia. For example, epidemiological studies have demonstrated with few exceptions that populations consuming large quantities of saturated fat and cholesterol have a relatively high concentration of serum cholesterol and a high mortality from coronary heart disease. Conversely, the serum cholesterol levels and the mortality from coronary disease are low in populations with a low consumption of saturated fat and cholesterol. While it is recognized that other factors can also contribute to the development of this disease there appears to be a continuous relationship between the concentration of serum cholesterol, coronary disease, and coronary mortality. It is also known that cholesterol accumulates in various parts of the circulatory system, atherosclerosis, or in soft tissues, xanthomatosis.

Various agents have been suggested and/or effectively used to lower plasma and total body cholesterol levels. These include nonabsorbable anion exchange resins such as Colestipol or Questran, plant sterol, e.g., β-sitosterol, linoleoyl amide and certain antibiotics. These agents act in varying degrees to block the absorption of dietary cholesterol or the enterohepatic flux of cholesterol, e.g., by binding cholesterol-rich bile salts (non-absorbable anion exchange resins). Plant sterols inhibit cholesterol takeup by the serum by decreasing its solubility in oily material which is necessary for absorption from the intestinal tract. Neomycin has been tested because of its digitonin-like cholesterol precipitating effect in the gastrointestinal tract. But the use of this antibiotic agent for controlling cholesterol levels in the body is not entirely suitable.

None of these agents is ideally acceptable for lowering cholesterol levels either because of undesirable side effects, too large amounts are required, or excessive amounts of carrier are required because of the properties of the agent.

Wright, et al., PROC. SOC. EXPL. BIOL. MED. 115, No. 2, pp. 497–502, postulate the use of mineral oil to provide means for extracting cholesterol from the intestinal tract, but note that because the solubility of cholesterol in mineral oil is low, very large amounts of mineral oil would have to be ingested in order to be effective.

U.S. Pat. No. 3,600,186 to Mattson, et al. discloses low calorie fat-containing food compositions in which, at least, a portion of the fat content is replaced with a sugar fatty acid ester, said fatty acid ester having at least four fatty acid ester groups with each fatty acid having from 8 to 22 carbon atoms.

U.S. Pat. No. 3,093,481, Eckey, et al. relates to plastic glyceride fats containing from about 0.01% to about 5% by weight of a fatty acid ester of a carbohydrate selected from the group consisting of oligosaccharides and dextrin whereby at least half of the hydroxyl groups of the carbohydrate are esterified with saturated fatty acids having from 14 to 22 carbon atoms. Said fatty acid esters improve the overall physical characteristics of shortening.

Thus, while the prior art teaches the use in food products of certain of the polyol esters employed in the present invention for various purposes, the pharmaceutical utility of such materials is not disclosed therein.

A more suitable pharmaceutical composition for inhibiting the absorption of cholesterol would be desirable.

SUMMARY OF THE INVENTION

The present invention is based, in part, upon the discovery that certain fatty esters, defined hereinafter, will inhibit the absorption of cholesterol. In more detail, these pharmaceutical compositions in unit dosage form comprise from about 0.1 gram to about 5 grams of a polyol fatty acid ester having at least four fatty acid ester groups, each fatty acid having from about eight to about 22 carbon atoms.

In its method aspect, the invention provides a method for treating or preventing hypercholesterolemia by inhibiting the absorption of cholesterol comprising administering to an animal an effective amount of a polyol fatty acid ester having at least four fatty acid ester groups, each fatty acid having from about eight to about 22 carbon atoms.

DETAILED DESCRIPTION OF THE INVENTION AND ITS PREFERRED EMBODIMENTS

The pharmaceutical compositions in unit dosage form contemplated in this invention comprise well-defined polyol fatty acid esters. The polyol starting material must have at least four esterifiable hydroxyl groups. Examples of suitable polyols are sugars, including monosaccharides and disaccharides, and sugar alcohols. Examples of monosaccharides containing four hydroxyl groups are xylose, and arabinose and the sugar alcohol derived from xylose, i.e., xylitol. The monosaccharide erythrose starting material is not suitable for the practice of this invention since it only contains three hydroxyl groups; but, the sugar alcohol derived from erythrose, i.e., erythritol, contains four hydroxyl groups and accordingly can be used. Suitable five hydroxyl group-containing monosaccharides are galactose, fructose, and sorbose. Six hydroxyl groups containing sugar alcohols derived from sucrose, glucose, and sorbose, e.g., sorbitol, are also suitable. Examples of disaccharide polyols which can be used include maltose, lactose, and sucrose, all of which contain eight hydroxyl groups.

Preferred polyols for preparing the esters for use in the present invention are selected from the group consisting of erythritol, xylitol, sorbitol, glucose and sucrose.

The polyol starting material having at least four hydroxyl groups must be esterified with a fatty acid having from about eight to about 22 carbon atoms. Examples of such fatty acids include caprylic, capric, lauric, myristic, myristoleic, palmitic, palmitoleic, stearic, oleic, ricinoleic, linoleic, linolenic, eleostearic, arachidic, arachidonic, behenic, and erucic acid. The fatty acids can be derived from naturally occurring or synthetic fatty aicds; they can be saturated or unsaturated, including positional and geometrical isomers, depending on the desired physical properties, for example liquid or solid, of the polyol fatty acid ester compound.

Fatty acids per se or naturally occurring fats and oils can serve as the source for the fatty acid component in the polyol fatty acid ester. For example, rapeseed oil provides a good source for $C_{22}$ fatty acid. $C_{16}$–$C_{18}$ fatty acid can be provided by tallow, soybean oil, or cottonseed oil. Shorter chain fatty acids can be provided by coconut, palm kernel, or babassu oils. Corn oil, lard, olive oil, palm oil, peanut oil, safflower seed oil, sesame seed oil, and sunflower seed oil, are examples of other natural oils which can serve as the source of the fatty acid component. Among the fatty acids, those that are preferred have from about 14 to about 18 carbon atoms, and are most preferably selected from the group consisting of myristic, palmitic, stearic, oleic, and linoleic fatty acids. Thus, natural fats and oils which have a high content of these fatty acids represent preferred sources for the fatty acid components, e.g., soybean oil, olive oil, cottonseed oil, corn oil, tallow and lard.

The polyol fatty acid esters useful in this invention must contain at least four fatty acid ester groups. Polyol fatty acid ester compounds that contain three or less fatty acid ester groups tend to be digested in the intestinal tract much in the manner as ordinary triglyceride fats, whereas the polyol fatty acid ester compounds that contain four or more fatty acid ester groups are substantially non-absorbable and non-digestable by the human body. It is not necessary that all of the hydroxyl groups of the polyol be esterified with fatty acid but it is preferable that the compound contain no more than two unesterified hydroxyl groups. Most preferably, all of the hydroxyl groups of the polyol are esterified with fatty acid, i.e., the compound is substantially completely esterified. The fatty acid ester groups can be the same or mixed on the same polyol molecule.

Thus, to illustrate the above points, sucrose triester of fatty acid would not be suitable for use herein because it does not contain the required four fatty acid ester groups. Sucrose tetra fatty acid ester would be suitable but is not preferred because it has more than two unesterified hydroxyl groups. Sucrose hexa fatty acid ester would be preferred because it has no more than two unesterified hydroxyl groups. An example of a highly preferred compound in which all of the hydroxyl groups are esterified with fatty acid is sucrose octa fatty acid ester. In any given polyol fatty acid ester compound, the fatty acid ester groups can be selected in view of the desired physical properties of the compound. The polyol compounds which contain unsaturated fatty acid ester groups and/or a preponderance of short chain, e.g., $C_{14}$, fatty acid ester groups are generally liquid at room temperature. The polyols esterified with long [e.g., $C_{14}$,]chain and/or saturated fatty acids, e.g., stearoyl, are generally solids at room temperatures.

The following are examples of suitable polyol fatty acid esters containing at least four fatty acid ester groups, suitable for use in the present invention. Glucose tetraoleate, glucose tetrastearate, glucose tetraester of soybean oil fatty acid, mannose tetraester of tallow fatty acids, galactose tetraester of olive oil fatty acid, arabinose tetraester of cottonseed oil fatty acid, xylose tetralinoleate, galactose pentastearate, sorbitol tetraoleate, sorbitol hexaester of olive oil fatty acid, xylitol pentapalmitate, xylitol tetraester of substantially completely hydrogenated cottonseed oil fatty acid, sucrose tetrastearate, sucrose pentastearate, sucrose hexaoleate, sucorse octaoleate, sucrose octaester of substantially completely hydrogenated soybean oil fatty acid, sucrose octaester of peanut oil fatty acid. As noted before, highly preferred polyol fatty acid esters are those wherein the fatty acids contain from about 14 to about 18 carbon atoms and are thus derived from such natural materials as soybean oil and olive oil. Examples of such compounds are erythritol tetraester of olive oil fatty acid, erythritol tetraoleate, xylitol pentaoleate, sorbitol hexaoleate, sucrose octaoleate, and sucrose octaester of soybean oil fatty acid.

The polyol fatty acid esters suitable for use in this invention can be prepared by a variety of methods well known to those skilled in the art. These methods include: transesterification with methyl, ethyl or glycerol fatty acid esters, acylation with a fatty acid chloride; acylation with a fatty acid anhydride and acylation with a fatty acid per se. As an example, the preparation of polyol fatty acid esters is described in U.S. Pat. No. 2,831,854.

Specific examples of the preparation of polyol fatty acid esters suitable for use in this invention follow hereinafter.

Erythritol tetraoleate — Erythritol and a 5-fold excess of ethyl oleate was heated under vacuum during mechanical agitation, in the presence of sodium methoxide catalyst over 2 several hour periods at about 180°C. The reaction product (erythritol tetraoleate) was refined in petroleum ether and crystallized three times from several volumes of acetone at 34°F.

Xylitol pentaoleate — Xylitol and a 5-fold excess of ethyl oleate in dimethylacetamide (DMAC) solution were heated in the presence of sodium methoxide catalyst during mechanical agitation under vacuum over a 5-hour period at about 180°C. During this time the DMCA was distilled off. The product (xylitol pentaoleate) was refined in petroleum ether solution and, after being freed of petroleum ether solution, was separated as a liquid layer 4 times from acetone at 34°F and twice from alcohol at 50°F.

Sorbitol hexaoleate was prepared by essentially the same procedure used to prepare xylitol pentaoleate except that sorbitol was substituted for xylitol.

Sucrose octaoleate was also prepared by essentially the same procedure as that used to prepare xylitol pentaoleate except that sucrose was substituted for xylitol.

The required dosage of the polyol fatty acid esters will vary with the severity of the condition and the duration of the treatment. Dosages can range from about 0.01 mg./kg. to about 500 mg./kg. (unless otherwise specified, the unit designated "mg./kg." as used herein refers to mg. of compound per kilogram of body weight), preferably from about 0.1 mg./kg. to about 125 mg./kg. with up to six dosages, preferably up to four dosages daily. Dosages greater than about 500 mg./kg. or daily dosages greater than about 1,000 mg./kg., although effective, may produce laxative effects. Dosages of less than about 0.1 mg./kg. do not materially inhibit the absorption of cholesterol. Most preferably, the doses are administered at meal times. The dosages are to be administered orally in any suitable unit dosage form such as pills, tablets, and capsules. Preferred are capsules made from gelatin.

As used herein, the term "pharmaceutical carrier" denotes a solid or liquid filler, diluent or encapsulating substance. Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar, alginic acid; pyrogen-free water; isotonic saline; ethyl alcohol and phosphate buffer solutions, as well as other non-toxic compatible substances used in pharmaceutical formulations. Wetting agents and lubricants such as sodium lauryl sulfate, as well as coloring agents, flavoring agents and preservatives, can also be present.

A pharmaceutical carrier is desirably employed in conjunction with the polyol fatty acid esters to provide desirable pharmaceutical compositions. Suitable carriers can provide a practical size to dosage relationship, composition forms which can be easily ingested and means for providing a very accurate unit dose in a convenient form. The pharmaceutical carrier can comprise from about 0.1% to 99% by weight of the total composition.

The following examples are illustrative of the invention.

EXAMPLE I

Gelatin capsules are prepared by conventional methods comprised as follows:

| Ingredients | Mg. per Capsule |
|---|---|
| Sucrose Octaoleate | 1500 |
| Starch | 20 |
| Sodium Lauryl Sulfate | 2.90 |

The above capsules administered orally 3 times daily (one with each meal) substantially inhibit cholesterol uptake and decrease the level of cholesterol in the circulatory system of a patient afflicted with hypercholesterolemia.

Similar results are obtained when the sucrose octaoleate is replaced with an equivalent quantity of a polyol fatty acid ester selected from the group consisting of glucose tetraoleate; glucose tetrastearate; glucose tetraester of soybean oil fatty acid; mannose tetraester of tallow fatty acid; galactose tetraester of olive oil fatty acid; arabinose tetraester of cottonseed oil fatty acid; xylose tetralinoleate; galactose pentastearate; sorbitol tetraoleate; sorbitol hexaester of olive oil fatty acid; xylitol pentapalmitate; xylitol tetraester of substantially completely hydrogenated cottonseed oil fatty acid; sucrose tetrastearate; sucrose pentastearate; sucrose hexaoleate; sucrose octaester of substantially completely hydrogenated soybean oil fatty acid; sucrose octaester of peanut oil fatty acid; erythritol tetraester of olive oil fatty acid; erythritol tetraoletate; xylitol pentaoleate; sorbitol hexaoleate; sucrose octaoleate; and sucrose octaester of soybean oil fatty acid.

What is claimed is:

1. A pharmaceutical composition in effective unit dosage amounts for inhibiting the absorption of cholesterol comprising from about 0.1 gram to about 5 grams of a polyol fatty acid ester having at least four fatty acid esters groups, wherein the polyol is selected from the group consisting of sugars and sugar alcohols containing from four to eight hydroxyl groups and wherein each fatty acid group has from about eight to about 22 carbon atoms.

2. A composition in accordance with claim 1 wherein the hydroxy groups of the polyol are all esterified.

3. A composition in accordance with claim 1 containing from about 0.5 gram to about 2 grams per unit dosage.

4. A composition in accordance with claim 5 wherein the esterified polyol is sucrose octaoleate.

5. A method for treating hypercholesterolemia by inhibiting the absorption of cholesterol comprising systemically administering to an animal susceptible to or afflicted with hypercholesterolemia successive therapeutically effective doses of a polyol fatty acid ester having at least 4 fatty acid esters groups, wherein the polyol is selected from the group consisting of sugars and sugar alcohols containing from four to eight hydroxyl groups and wherein each fatty acid group has from about eight to about 22 carbon atoms.

6. The method of claim 5 wherein the hydroxy groups of the polyol are all esterified.

7. The method of claim 6 wherein the doses are unit doses containing from about 0.5 gram to about 5 grams per unit dose.

8. The method of claim 7 wherein the unit doses are from about 0.5 to 2 grams per unit dose.

9. The method of claim 8 wherein the esterified polyol is sucrose octaoleate.

* * * * *

UNITED STATES PATENT OFFICE
CERTIFICATE OF CORRECTION

PATENT NO. : 3,954,976
DATED : May 4, 1976
INVENTOR(S) : Fred Hugh Mattson and Robert Anthony Volpenhein It is certified that error appears in the above-identified patent and that said Letters Patent are hereby corrected as shown below:

Page 1, under "ABSTRACT OF THE DISCLOSURE", line 6, delete "systematically" and insert therefor -- systemically --.

Column 6, line 4 of Claim 1, after "of a" insert -- non-absorbable and non-digestible --.

Column 6, line 5 of Claim 1, delete "esters" and insert therefor -- ester --.

Column 6, line 1 of Claim 4, delete "Claim 5" and insert therefor -- Claim 3 --.

Column 6, line 5 of Claim 5, after "of a" insert -- non-absorbable and non-digestible --.

Column 6, line 6 of Claim 5, delete "esters" and insert therefor -- ester --.

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*